United States Patent
Henry et al.

(10) Patent No.: US 7,366,566 B2
(45) Date of Patent: Apr. 29, 2008

(54) AUTOMATIC COMMUTATIONS OF AAI/DDD MODE IN THE PRESENCE OF PAROXYSTIC AVB IN AN ACTIVE IMPLANTABLE MEDICAL DEVICE, IN PARTICULAR A CARDIAC PACEMAKER

(75) Inventors: Christine Henry, Paris (FR); Marcel Limousin, Paris (FR); Amel Amblard, Chatenay Malabry (FR)

(73) Assignee: ELA Medical S.A.S., Montrouge (FR)

( * ) Notice: Subject to any disclaimer, the term of this patent is extended or adjusted under 35 U.S.C. 154(b) by 284 days.

(21) Appl. No.: 11/022,326

(22) Filed: Dec. 22, 2004

(65) Prior Publication Data

US 2005/0143780 A1 Jun. 30, 2005

(30) Foreign Application Priority Data

Dec. 29, 2003 (FR) .................................. 03 15517

(51) Int. Cl.
*A61N 1/362* (2006.01)

(52) U.S. Cl. .......................................................... 607/9

(58) Field of Classification Search ...................... 607/9
See application file for complete search history.

(56) References Cited

U.S. PATENT DOCUMENTS 5,318,594 A * 6/1994 Limousin et al. .............. 607/9
5,893,882 A 4/1999 Peterson et al. ............. 607/14
6,343,231 B1 * 1/2002 Bouhour et al. ............... 607/9
2003/0078627 A1 4/2003 Casavent et al. .............. 607/9
2004/0010292 A1 * 1/2004 Amblard et al. ............... 607/9
2004/0143299 A1 * 7/2004 Casavent et al. .............. 607/9

FOREIGN PATENT DOCUMENTS

EP 0 488 904 A1 11/1991
EP 1 346 750 A1 3/2003

* cited by examiner

*Primary Examiner*—George R. Evanisko
*Assistant Examiner*—Joseph Stoklosa
(74) *Attorney, Agent, or Firm*—Orrick Herrington & Sutcliffe, LLP

(57) ABSTRACT

A device including circuits able to control the switching of a AAI mode in a DDD mode, and conversely the return of DDD mode to AAI mode, according to predetermined criteria of detection of atrio-ventricular block (AVB) of the first, second, or third degree and of ventricular pause. The device includes moreover circuits for detecting state, able to diagnose at least a specific temporary state of the patient, in particular a state of effort or sleep, and the circuits for mode switching operate in response to these circuits for detecting state to modify selectively, for the length of time when the aforementioned state is diagnosed, the criteria of switching from AAI mode towards DDD mode and/or the criteria of return to AAI mode, and/or the criteria of final commutation in DDD mode.

27 Claims, No Drawings

AUTOMATIC COMMUTATIONS OF AAI/DDD MODE IN THE PRESENCE OF PAROXYSTIC AVB IN AN ACTIVE IMPLANTABLE MEDICAL DEVICE, IN PARTICULAR A CARDIAC PACEMAKER

FIELD OF THE INVENTION

The present invention relates to "active implantable medical devices" as defined by the Jun. 20, 1990 directive 90/385/CEE of the Council of the European Communities, and more particularly to cardiac pacemakers, "multisite devices" (triple or quadruple chambers), defibrillators, and/or cardiovertors that are able to deliver to the heart pulses of low energy for treatment of disorders of cardiac rhythm.

BACKGROUND OF THE INVENTION

The invention more particularly relates to those devices that include circuits of stimulation and detection at the same time on the atrium and on the ventricle, and that can operate according to at least two operating modes, DDD or AAI. These devices can be equipped with a mode called "AAISafeR," which ensures an automatic commutation from DDD mode to AAI mode and vice versa.

The basic operating mode of a DDD/AAI pacemaker is an AAI mode, with an atrial stimulation and a monitoring (detection) of the ventricular activity. This mode is maintained as long as atrio-ventricular conduction is normal, i.e., as long as each atrial event (atrial detection, corresponding to a spontaneous activity, or atrial stimulation) is followed by an associated ventricular detection.

In certain circumstances, however, atrio-ventricular blocks (AVB) can appear, involving a temporary disorder of depolarization of the ventricle. When this happens, the pacemaker switches automatically to DDD mode, with parameters optimized for the temporary AVB situation. After disappearance of the AVB, and thus re-establishment of atrio-ventricular conduction, when a certain number of conditions are filled the pacemaker turns over automatically to AAI mode. This commutation between DDD and AAI modes is described in EP-A-0 488 904 and its counterpart, U.S. Pat. No. 5,318,594 (incorporated herein by reference), and EP-A-1 346 750, its counterpart U.S. Patent App. No. US2004010292, all of which are assigned commonly herewith to ELA Médical, as well as in U.S. Patent Application Nos. 20020082646 and 20030078627, which are assigned to Medtronic, Inc.

The starting point of the present invention lies in observations carried out at the time of a clinical follow-up of patients equipped with DDD/AAI devices with automatic mode commutation (also called automatic mode switching). It appeared that these apparatuses have an insufficient specificity according to the type of AVB, so that in certain cases inappropriate commutations were occurring towards DDD mode, leading to unjustified alternations of commutations AAI towards DDD then DDD towards AAI, or to final commutations, in DDD mode, which were useless. More precisely, one classically distinguishes three degrees of AVB, corresponding to an increasing gravity of the disorder of conduction:

a) The AVB of the first degree (AVB1) corresponds to a conduction present, but delayed; the commutation towards DDD mode is started when the number of atrial events followed by a ventricular detection occurring after a delay longer than, e.g., 350 ms (for a spontaneous atrial event) or 450 ms (for a stimulated atrial event) exceeds a given number, e.g., in the event of detection of six consecutive cardiac cycles fulfilling this criterion.

b) The AVB of the second degree (AVB2) is characterized by an incomplete conduction, the progressive lengthening of the interval PR (or AR) being such that a part of the P waves are no longer conducted. Commutation to DDD mode on an AVB of the second degree is typically started when the number of atrial events not followed by a ventricular detection exceeds a certain number over the duration of a window of monitoring extending over a predetermined number of atrial events. In other words, commutation to, e.g., DDD is started when the device detects three nonconsecutive blocked P waves among the last twelve cardiac cycles.

c) The complete AVB, or AVB of the third degree (AVB3), which is the most serious, appears by atrial waves (stimulated or spontaneous) completely blocked, i.e., which are not followed any more by ventricular depolarization; the device must then quickly operate the commutation to DDD mode, this commutation intervening typically when it detects a succession of two blocked atrial waves (detected or stimulated), or if it times out by more than three seconds without ventricular detection.

It also is necessary to take into account:

d) The ventricular pause, which may find its origin in a disorder of atrio-ventricular conduction. There is ventricular pause when the interval separating two ventricular events exceeds a given time, e.g., exceeds three seconds.

After a commutation to DDD mode on an AVB, to return to AAI mode the device waits until a certain number of return criteria are fulfilled, e.g., it returns to AAI mode after one hundred cycles with ventricular stimulation (in order to be able to test, while returning to AAI mode, if a spontaneous atrio-ventricular conduction is restored) or twelve consecutive cycles with detection of a spontaneous depolarization of the ventricle. In addition, it may be desirable to envisage a limitation of the number of successive commutations from AAI towards DDD over a given period. If, e.g., the device started more than fifteen commutations over a 24 hour period or if, over a three consecutive day period, the device started more than five commutations over 24 hours, then it switches definitively to DDD mode and functions on the basis of a programmed parameter of stimulation (in particular the atrio-ventricular delay), this configuration being preferably maintained until there is a new examination of the patient and possible reprogramming by the physician. The above-identified rules of commutation may, however, in certain cases be inappropriate.

The first case is that of "troubles of the atrial rate" (TdRA), a generic term which covers various atrial arrhythmias (nonphysiological episodes of acceleration of the rate) such as tachycardia, fibrillation, flutter, etc., which are all characterized by detection of a fast atrial rate. In such a case of suspected or proven TdRA, the above criteria of detection of AVB1, AVB2, or AVB3 are no longer appropriate because the same cardiac cycle generally lets several atrial events appear, and the multiple detections distort the analysis of atrio-ventricular conduction. On the other hand, the criterion of detection of ventricular pause remains relevant.

In addition, the AVB very often presents an intermittent character, particularly the AVB1 and AVB2, which can, in certain situations, present a simply paroxystic character, i.e., they can occur commonly, in particular during phases of effort or during sleep, and disappear spontaneously at the end of the effort or upon awakening. In these situations of paroxystic AVB, with the known devices functioning in the manner indicated, one can note a certain number of disadvantages:

A final commutation in DDD mode on detection of paroxystic AVB at night is not a priori relevant because the patient can also present a satisfactory atrio-ventricular conduction during the day or at rest.

During a same phase of effort, it would be desirable to avoid successions of commutations AAI towards DDD then DDD towards AAI. Indeed, if there were, e.g., a commutation AAI towards DDD during the effort, one can reasonably think that the AVB that started this commutation will persist until the end of the effort, and that attempts at re-commutation in AAI are not suitable as long as the effort persists, because they are likely to involve symptomatic pauses at the time of this exercise.

On the other hand, when the effort is finished, it is desirable to be able to return as quickly as possible to an AAI operation because, if the AVB were only paroxystic, the A-V conduction should normally reappear.

It can be excessive to generate a final commutation after successive commutations very close from/to each other (in the event of an episode of conduction disorder), because this episode can be unique over a given period, e.g., an episode of block during one hour duration over one day.

In addition, little clinical information being available on the "paroxystic" character of the AVB (their duration, in particular, is little known), it may be excessive to operate a final commutation caused by a succession of commutations happening during the same episode of conduction. It is necessary, however, to discriminate the chronic AVB, in order to be sure that the apparatus will end up with a commutating to the DDD mode if the conduction disorder episode lasts several days.

Finally, during the effort the heartbeat rate accelerates, and from a hemodynamic view it is not desirable to let the interval PR (or AR) lengthen up to 350 ms (or 450 ms) before starting commutation towards DDD mode. These values of 350 or 450 ms are programmable, but they are fixed whatever the frequency and do not account for the detection of an AVB1, for the particular state of the patient, in phase of effort or not.

OBJECTS AND SUMMARY OF THE INVENTION

The present invention proposes to resolve these difficulties while bringing an improvement to the known devices by an appropriate adjustment of the mode commutation.

More precisely, one of the goals of the invention is to introduce a selectivity into operation so as to, on the one hand, manage in a particular way the case of the paroxystic AVB and, on the other hand, ensure a fine management, taking account at the same time of the type of AVB and of the circumstances surrounding the occurrence of this AVB.

Another goal of the invention is to avoid inappropriate final commutations in the event of detection of AVB during an effort by the patient or while the patient is at sleep.

A further goal of the invention is to avoid inappropriate successive commutations likely to unnecessarily involve a final commutation in DDD mode.

Yet another goal of the invention is to manage in a finer way the final commutation in DDD mode by operating a preliminary durable commutation that is non-final, in DDD mode, the commutation becoming final only if particular criteria are fulfilled.

Another goal of the invention is to manage the return towards AAI mode in a more effective way from the hemodynamic view if the patient is in a particular temporary state such as effort or sleep, or in other diagnosed states, such as a phase of cardiac decompensation or a phase of arrhythmia.

The type of device to which the invention applies is a device DDD with Automatic Mode Switching of a known type, e.g., according to EP-A-0 488 904 or EP-A-1 346 750 and their U.S. counterparts, identified above, including means for detecting spontaneous atrial and ventricular events, means for ventricular and atrial stimulation, means able to operate the device in AAI mode with ventricular detection, and means able to operate the device in DDD mode, and means for mode switching, able to control according to predetermined criteria the switching from AAI mode in DDD mode, and conversely the return from DDD mode to AAI mode. These predetermined criteria also include criteria of return to AAI mode after switching towards DDD mode.

In one embodiment of the invention, the device includes means for detecting a state of the patient able to diagnose a temporary specific state of the patient carrying the device, these means being able to diagnose at least a phase of effort and/or a phase of sleep of the patient and a length of time of said temporary specific state, and the means for mode switching are means operating in response to the state detecting means to modify the aforementioned criteria of switching from AAI mode towards DDD mode for the length of time during which the aforementioned state is diagnosed.

The criteria of switching from AAI mode towards DDD mode are in particular criteria able to control the switching when at least one of the following conditions is fulfilled:

a) the number of atrial events followed by a ventricular detection occurring after a time longer than a first reference duration exceeds a first predetermined number;

b) the number of atrial events not followed by a ventricular detection exceeds a second predetermined number among a third given number of consecutive atrial events;

c) the number of consecutive atrial events not followed by a ventricular detection exceeds a fourth predetermined number; and d) the interval separating two ventricular events exceeds a second reference duration.

A first particular aspect of the invention relates to the taking into account of states other than sleep and effort. For that, the state detecting means can diagnose in addition a phase of cardiac decompensation of the patient and/or a phase of arrhythmia of the patient and/or a phase of suspicion of disorder of the atrial rate of the patient. In the latter case, the means for mode switching can suspend, for a length of time at least equal to the duration of the phase of suspicion of disorder of the atrial rate of the patient, the checking of the conditions a) to c) of the criteria of switching from AAI mode towards the DDD mode, while maintaining the checking of the condition d).

A second particular aspect of the invention relates to the presence of counters making it possible to ensure a differentiated management of the switching of mode. For this purpose, it is envisaged to provide a grid of counters assigned respectively to conditions a) to d) of the criteria of switching from AAI mode towards DDD mode and to the types of states likely to be diagnosed, the corresponding counter being incremented when the respective condition is fulfilled and when the type of respective state is detected. It can in particular be envisaged to provide a grid of thresholds homologous with the grid of counters, each threshold being programmable, to force the switching from AAI mode towards DDD mode when at least one of the thresholds is reached by the corresponding counter.

A third particular aspect of the invention relates to the opposite commutation from DDD towards AAI. For this purpose, the mode switching means operate in response to the state detecting means to modify the aforementioned criteria of return to AAI mode after switching towards DDD mode during the time when a phase of effort or sleep is diagnosed, more precisely:

during the time when a phase of effort or sleep is diagnosed, to temporarily suspend any return to AAI mode after switching towards DDD mode, or to temporarily modify in a restrictive direction the aforementioned criteria of return to AAI mode after switching towards DDD mode; and/or after the end of the aforementioned phase of effort or sleep, to control without delay the return to AAI mode after switching towards DDD mode, or to temporarily modify in an extensive direction the aforementioned criteria of return to AAI mode after switching towards DDD mode.

A fourth particular aspect of the invention relates to the possibility of operating a durable commutation in DDD mode. The predetermined criteria then include criteria of durable commutation in DDD mode, and the means for mode switching include means of durable commutation, able to inhibit the return from DDD mode to AAI mode and to force the operating mode to DDD mode as a function of the aforesaid criteria of durable commutation. The means of durable commutation can in particular include counters incremented selectively according to conditions a) to d) of the criteria of switching from AAI mode towards DDD mode when the respective condition is fulfilled, and means to inhibit the return from DDD mode to AAI mode and to force the operating mode to DDD mode when the counters reach a predetermined counting configuration. Preferably, the means of durable commutation inhibit the incrementing of the counters:

when one of conditions a) to c) is fulfilled while authorizing the incrementing when condition d) is fulfilled, in the event of commutation consecutive to a diagnosis of phase of effort or sleep; or in the event of the occurrence of a commutation separated from a preceding commutation by a number of cycles in AAI mode lower than a fifth predetermined number.

The means of durable commutation also preferably inhibit the return from DDD mode to AAI mode and force the operating mode to DDD mode when:

the number of commutations of AAI mode towards DDD mode is higher than a sixth predetermined number over a first predetermined temporal period, or the percentage of ventricular events stimulated over a second predetermined temporal period is higher than a first predetermined threshold.

Advantageously, the means of durable commutation control the return to the operating mode in AAI mode, and, if necessary, re-initialize the counters at the end of each phase of sleep.

A fifth particular aspect of the invention relates to the possibility of controlling a commutation no longer durable, but final, towards DDD mode. The predetermined criteria then include criteria of final commutation in DDD mode, and the means for mode switching include means for final commutation, able to prohibit the return from DDD mode to AAI mode and to impose an operating DDD mode until reprogramming of the device, as a function of the aforesaid criteria for final commutation, in particular when:

the number of durable commutations of AAI mode towards DDD mode is higher than a seventh predetermined number over a third predetermined temporal period, or the percentage of ventricular events stimulated over a fourth predetermined temporal period is higher than a second predetermined threshold.

A sixth particular aspect of the invention relates to the particular management of commutations during an effort. With this aim, the means for mode switching reduce the aforementioned first reference duration during the time when a phase of effort is diagnosed. This reduction can in particular be a reduction with a value that is an inverse function of the frequency of stimulation, in particular a monotonic decreasing function from the base frequency of stimulation to the maximum frequency of stimulation. Advantageously, the function is decreasing from a low frequency, higher than the base frequency of stimulation, until a high frequency, higher than the maximum frequency of stimulation, and is constant below the base frequency of stimulation and above the maximum frequency of stimulation.

A seventh particular aspect of the invention relates to the possibility of recording specific data, making it possible to document atrio-ventricular conduction for later diagnosis. For this purpose, the device includes means for differentiated recording of cardiac data, able to memorize specifically certain predetermined data during the time when the aforementioned specific state, temporary, is diagnosed. These data can in particular include the values of the durations of atrio-ventricular conduction, or the duration of episodes during which commutations follow each other separated from one another by number of cycles in AAI mode lower than a fifth predetermined number.

DETAILED DESCRIPTION OF THE INVENTION

One now will describe an example of realization of the device of the invention, which can be implemented by suitable programming of the control software of a known pacemaker of double chamber type integrating a DDD mode and an AAI mode with monitoring of the ventricular activity.

Suitable devices for which the present invention has application include, e.g., the active implantable medical devices available from ELA Médical, Montrouge, France. These devices are microprocessor-based systems having circuits for receiving, conditioning and processing detected electrical signals, and are capable of receiving software instructions by telemetry, storing them in memory, and then executing those instructions to perform the functions described above in implementing the invention. The creation of suitable software instructions for controlling an implant to perform the aforementioned functions of the present invention are within the abilities of a person of ordinary skill in art.

Definitions and Operation Depending on the State of the Art

One first of all will give a number of definitions used in describing the present invention.

Detection P: sensing of a spontaneous activity (P-wave) having its origin in the atrium; it will be considered that there is indeed P detection if this one is not followed in a given delay, e.g., in 31 ms, by a ventricular detection (if not, one would be in a ventricular situation of "far-field", i.e., of sensing via the atrium a remote depolarization coming from the ventricle);

Detection R: sensing of a spontaneous activity (R-wave) having its origin in the ventricle;

Stimulation A: stimulation delivered to the atrium;

Stimulation V: stimulation delivered to the ventricle;

Atrial event: P detection or A stimulation;

Cardiac cycle: interval of time separating two events of comparable nature in the same cavity, e.g., separating two detections P, or two stimulations A; and PR Delay (or AR delay): atrio-ventricular conduction delay, i.e., interval of time separating a spontaneous (P) or stimulated atrial depolarization (A) from a consecutive induced spontaneous ventricular depolarization (R).

At the beginning, the operation of the pacemaker is an operation in AAI mode with monitoring of the ventricular activity: the algorithm seeks the presence or absence of a ventricular activity, which in this last case could lead to suspect an AVB, so as to, if required, switch to DDD mode of double chamber stimulation with atrio-ventricular association, i.e., with calculation and application of an atrio-ventricular delay for the controlled stimulation of the ventricle. In this AAI mode, the ventricular absence of activity is accepted on a given number of cycles without a ventricular stimulation not being started. This number is programmable, e.g., 2 cycles.

As discussed above, four situations can induce the passage to DDD mode:

1) an atrio-ventricular block of first degree (AVB1), which appears by a time of atrio-ventricular conduction higher than a given value, typically 350 ms, after a detection P or 450 ms after a stimulation A. The commutation in DDD mode intervenes, typically after six consecutive cycles;

2) an atrio-ventricular block of the second degree (AVB2), which appears by a ratio: number of non-extra systolic P waves/number of non-extra systolic waves R, greater than 1. The commutation intervenes if, typically, the apparatus detects a ratio equal to or higher than 12/9 (3 blocked P waves on the last 12 cycles);

3) a complete atrio-ventricular block (AVB3), which appears by blocked atrial waves (stimulated or spontaneous), i.e., atrial depolarization not followed by ventricular depolarization. Typically, the commutation intervenes if the apparatus detects a succession of two blocked atrial waves (detected or stimulated).

4) a ventricular pause, which appears if more than three seconds passed without ventricular detection, independently from the point of knowing if this pause results, or not, in a disorder of atrio-ventricular conduction.

In the presence of one of these criteria, the device switches from AAI mode to DDD mode.

After return of a spontaneous ventricular activity during a certain number of cycles, e.g., after 12 detections R, or a predetermined number of cycles in DDD mode, e.g., 100 cycles with V stimulation, the device then turns from DDD into AAI mode and remains in AAI mode as long as none of the three above mentioned criteria of commutation of AAI towards DDD is fulfilled. In addition, to limit the number of successive commutations of AAI towards DDD over a given period, the device switches definitively to the DDD mode, with parameter programmed, if, for example:

the number of commutations AAI towards DDD over one 24 hour period exceeds a maximum number authorized, e.g., 15 commutations, or during three consecutive days, the daily number of commutations AAI towards DDD exceeds a maximum number authorized, e.g., 5 commutations over 24 H.

This known operating mode is modified according to the present invention in the manner to be described.

Detection of the Troubles of the Atrial Rate and Other Particular States

A first improvement consists in detecting the appearance or the risk of appearance (suspicion) of troubles of the atrial rate (TdRA). Indeed, TdRA is characterized by the presence of several atrial depolarizations during the same cycle, which causes distortion of the criteria of detection of AVB1, AVB2, and AVB3, described above, based on analysis of atrio-ventricular conduction. The ventricular pause criterion, which does not utilize the occurrence of an atrial event, remains on the other hand valid. TdRA can be detected by an algorithm such as that described in EP-A-0 755 696 and its counterpart, U.S. Pat. No. 5,713,928 (incorporated herein by reference), commonly assigned herewith to ELA Médical, which explains in particular the manner of discriminating between isolated atrial extra systoles (AES) and TdRA themselves by a detection in two times: phase of suspicion of TdRA, followed by a phase of confirmation of TdRA.

Within the framework of this invention, detection according to the above described criteria of AVB1, AVB2, and AVB3 is suspended as soon as the algorithm enters the phase of suspicion of TdRA. During the phase of suspicion, only the ventricular pause criterion is likely to cause a commutation of the device to DDD mode.

In the event of confirmed TdRA, the apparatus commutates in DDD mode of fallback operating mode. If, on the other hand, the phase of suspicion of TdRA does not lead to confirmation of TdRA (i.e., probably where there was isolated AES), the criteria of detection of AVB1, AVB2, and AVB3 are restored, preferably after some cycles, i.e., the criteria of detection of AVB1, AVB2, and AVB3 will be suspended during all the phase of suspicion to N cycles after the end of suspicion of TdRA.

The teaching of the present invention is also applicable in states other than TdRA that are likely to be diagnosed by the device, in particular the phases of cardiac decompensation, where the bad momentary hemodynamic state of the patient is detected by a measurement of intracardiac impedance or a measurement of intra-cavitary acceleration operated by a sensor integrated into the probe. It can also be a question of a phase of arrhythmia diagnosed by a dedicated algorithm of analysis of rate of heartbeat, for example the algorithm described in EP-A-0 838 235 and its counterpart, U.S. Pat. No. 5,868,793 (incorporated herein by reference), commonly assigned herewith to ELA Médical.

Differentiated Management of the Commutation of AAI in DDD

A second improvement consists in controlling in a differentiated way the commutation to DDD mode, on the one hand according to the type of disorder met (AVB1, AVB2, AVB3, or pause), and on the other hand according to the circumstances of the occurrence of this disorder, i.e., according to the state of the patient (effort, sleep, or other). Indeed, the commutations to DDD on certain types of AVB, or in certain circumstances, are not appropriate.

Such is the case of a patient implanted for AVB1, where the device would switch quickly, and then definitively, to DDD mode—in an inappropriate way taking into account the low severity of the AVB1 and its often sporadic nature. In the same way, a patient presenting a normal conduction at rest but an asymptomatic AVB1 during effort or at sleep would see the device commutating regularly in DDD during these periods with in the long term, if these commutations are too numerous, a final commutation in DDD mode—whereas the patient could have profited from AAI mode at least for the periods of rest. To take account of these circumstances, the device of the present invention includes means for detecting effort and/or sleep.

The detection of an effort can be carried out, in a way in itself known, by means of a sensor of activity, typically an accelerometer, making it possible to quickly detect a change of the activity of the carrier of the apparatus, as taught, e.g., in EP-A-0 550 293 and its counterpart, U.S. Pat. No. 5,330,510 (incorporated herein by reference), commonly assigned herewith to ELA Médical, or by means of a physiological combination of sensors and activity, as taught, for example, in EP-A-0 750 920 and its counterpart, U.S. Pat. No. 5,722,996 (incorporated herein by reference), commonly assigned herewith to ELA Médical, mentioned above.

As for the detection of sleep, it can be carried out by various techniques, in themselves known, of discrimination between awakening and sleep. The simplest technique consists of using an internal clock of the device, and commutating an indicator at fixed hours. It also is possible, as taught by EP-A-0 719 568 and its counterpart, U.S. Pat. No. 5,622,428 (incorporated herein by reference), commonly assigned herewith to ELA Médical, to operate a discrimination between awakening and sleep by analysis of a physiological signal of minute-ventilation (MV): indeed, the circadian variation of the frequency and the amplitude of the successive respiratory cycles of the patient is well reproduced by the signal MV; a calculation of average ventilation over 24 hours thus makes it possible to operate a satisfactory discrimination between a ventilation of awakening and a ventilation of sleep. One can also use a sensor of activity, typically an accelerometer (sensor G), whose signal makes it possible to detect the movements of the patient; the information of this type of sensor is not in itself not very specific regarding phases of awakening and sleep, but one can combine the signals delivered by a sensor G and a sensor MV to deduce meaningful information, as described, e.g., in EP-A-0 750 920 and its counterpart, U.S. Pat. No. 5,722,996 (incorporated herein by reference), commonly assigned herewith to ELA Médical, and EP-A-0 770 407 and its counterpart, U.S. Pat. No. 5,766,228 (incorporated herein by reference), commonly assigned herewith to ELA Médical.

In addition, to allow a differentiated commutation according to the detected disorder and circumstances from the occurrence from the disorder, the device comprises a grid of counters where each type of disorder (AVB1, AVB2, AVB3, or pause) is associated with a circumstance of the occurrence (e.g., effort, sleep, or other)—this means twelve criteria with each one an independently incrementable counter. The commutations AAI towards DDD are then programmed separately on each one of these twelve criteria, by prohibiting or authorizing the switching in DDD for each of the twelve criteria. In addition, when the switching to DDD is authorized, the threshold for release of the switching (crossing of the threshold by the associated counter) can be different for each criterion. Preferably, the device does not commutate to DDD mode on detection of an AVB1 (and this, whatever the state of the patient). It also does not commutate to DDD in the event of AVB2 at night. On the other hand, commutation to DDD is authorized for any AVB2 except during sleep, for any AVB3, or for any pause. These conditions can be summarized by the following truth table:

TABLE 1

|  | AVB1 | AVB2 | AVB3 | pause |
| --- | --- | --- | --- | --- |
| effort | Non | towards DDD | towards DDD | towards DDD |
| sleep | Non | Non | towards DDD | towards DDD |
| other | Non | towards DDD | towards DDD | towards DDD |

Differentiated Management of the Opposite Commutation from DDD to AAI

A third improvement consists in, when the device is commutated to DDD mode, modifying the management of the opposite commutation of return in AAI mode for particular states of patient, and this for the length of time when these states remain present. These particular states can be, like previously, the effort or sleep states (the teaching of the invention also being applicable to other particular states, in particular phases of cardiac decompensation or phases of arrhythmia). Thus, when a commutation AAI towards DDD takes place during an effort, the invention will inhibit the return to AAI mode or temporarily modify the criteria in a more restrictive direction, as long as the effort lasts. Indeed, if there were, e.g., commutations during the effort, one can think that the AVB will persist until the end of the effort, and attempts at re-commutation in AAI as long as this effort persists are not suitable, because such attempts are likely to involve symptomatic pauses during this effort.

When the effort is finished, it is, on the other hand, desirable to be able as fast as possible to find an operation AAI (since conduction is become again a priori normal) and thus to force the re-commutation towards AAI mode. Conversely, once the end of effort will have been detected, the present invention proposes to force the re-commutation to AAI mode as of detection of this end of effort, or to facilitate this re-commutation by temporarily modifying the criteria of re-commutation in an extensive direction.

More precisely, e.g., on a commutation AAI towards DDD occurring on detection of a AVB1 or AVB2 during an effort, or after a predetermined number of commutations AAI towards DDD on AVB1 or AVB2 during an effort, the criteria of return to AAI mode can be modified in the following way:

return to AAI suspended until the end of the effort (i.e., one remains in DDD mode as long as this effort lasts); or return to AAI authorized on a restrictive criterion, for example, 30 consecutive cycles—instead of 12—with R detection.

Conversely, when the end of effort is detected, the criteria of return to AAI mode can be modified, e.g., in the following way:

immediate and unconditional return to AAI mode; or return to AAI mode authorized in the presence of 6 consecutive cycles—instead of 12—with R detection, or after only 10 cycles—instead of 100—with ventricular stimulation.

The criteria above can apply independently or jointly in relation with the criteria of commutation during the effort on detection of AVB1, AVB2, AVB3, or of pause.

Durable Commutation in DDD Mode

A fourth improvement consists in controlling the final commutation so as to take account of the state of the patient and the circumstances surrounding the occurred commutations. One will understand by "durable commutation" a state in which the algorithm of piloting inhibits the return from DDD mode to AAI mode, and thus forces the operating mode to DDD mode, at least for a minimal predetermined length of time—thus leaving with the device an eventual possible automatic return to AAI mode. This durable commutation could be transformed later on into a "final commutation," where the return of DDD mode to AAI mode will be prohibited, DDD mode then being imposed until reprogramming of the device, without possibility of return to AAI mode.

The device includes, in addition to the means of detecting the effort or the sleep (see above), a grid of counters of commutation assigned to the four criteria having been able to start a switching from AAI mode towards DDD mode (AVB1, AVB2, AVB3, or pause) and to the states likely to be diagnosed (effort, sleep, or other). The device starts a durable commutation to DDD mode when the counters reach a predetermined configuration of counting. Because the unit is programmable, the physician has the freedom to manage the conditions of durable commutation.

It is in particular desirable to prevent a durable commutation in certain cases, i.e., the incrementing of the corresponding counter(s) will not be able to cause a durable commutation. Such is the case in particular of the commutations during effort or at sleep: they can be commutations on AVB1 only, or commutations on AVB2 and AVB3, or commutations on any particular combination of the criteria of AVB. The commutations on criteria of pause on the other hand will be taken into account to allow a durable commutation in DDD mode.

In the same way, it is desirable not to take into account non-isolated commutations, a non-isolated commutation being defined as a commutation separated from the preceding commutation by a number of cycles in AAI lower than a given number, typically a commutation separated from the preceding one per less than 100 cycles in AAI mode.

The device operates a durable commutation in DDD mode if, e.g., the number of commutations actually taken into account by the counters above is greater than a threshold over a given period, for example, more than fifteen commutations over 24 hours, or more than five commutations by 24 hours over three consecutive days. It is also possible to take into account as criterion of durable commutation the percentage of ventricular events stimulated over a given period (e.g., 24 hours). If this percentage exceeds a certain threshold, the apparatus starts a durable commutation to DDD mode even if the counters did not yet reach the configuration of counting which, if not, would have started this durable commutation.

Final Commutation to DDD Mode

A fifth improvement of the invention consists in controlling a commutation no more durable, but final, towards DDD mode. For this purpose, after one or more durable commutations the device examines whether there is, or is not, time to transform this durable commutation into a final commutation. For example, at each end of phase of sleep the device examines whether the current mode is a DDD mode due to a durable commutation. If such is the case, the device switches again in AAI mode, by re-initializing all the counters of durable commutation. If this phenomenon repeats N consecutive days (or if the percentage of stimulated ventricular events is higher than a given threshold on N consecutive days), then the device switches definitively to DDD, and this final commutation could be changed only by reprogramming of the apparatus by an physician.

Particular Management of Commutations During the Effort

A sixth improvement of the invention consists in replacing the durations of typical fixed references of 350 or 450 ms (PR or AR delay of reference for the detection of a AVB1) by one adjustable duration according to the state of the patient, more precisely a duration which can adapt during the effort. Indeed, in the event of effort, the rate of heartbeat increases and the typical fixed values of 350 or 450 ms appear too long, because it is not desirable, on a hemodynamic view, to leave the interval PR or AR to lengthen up to 350 or 450 ms before commutating with DDD mode. For that, the invention proposes to use for the PR interval of reference a PR(f) value adaptable during the effort, decreasing according to the heart rate F. One can, e.g., envisage for the interval PR of reference a linear law of variation on an interval delimited by two frequencies $f_{inf}$ and $f_{sup}$, in accordance with the following relation:

$$PR(f)=PR(f_{inf})-[(f-f_{inf})\times[(PR(f_{inf})-PR(f_{sup})]/(f_{sup}-f_{inf})], \text{ with, e.g., } PR(f_{inf})=350 \text{ ms et } PR(f_{sup})=250 \text{ ms.}$$

One can choose for $f_{inf}$ and $f_{sup}$, respectively, the base frequency of stimulation and the maximum programmed frequency of stimulation for the apparatus, e.g., $f_{inf}=f_{base}=30$ bpm and $f_{sup}=f_{max}=83$ bpm.

In the alternative, it is also possible to choose for $f_{inf}$ and $f_{sup}$ fixed frequencies, for example $f_{inf}=60$ bpm and $f_{sup}=150$ bpm. In this case, for $f=f_{inf}$, the value of the interval of reference will be constant (typically $PR=PR_{inf}=350$ ms), in the same way for $f=f_{sup}$ (typically $PR_{sup}=250$ ms) with a continuous linear variation between these two values.

The above formula can be transposed to calculation of the AR interval of reference, with $AR(f)=PR(f)+x$ ms (where x can be a constant value, e.g., 100 ms, or a variable value, e.g., a function of the heart rate).

Documentation of Atrio-Ventricular Conduction

A seventh improvement consists in the monitoring in a differentiated way the spontaneous atrio-ventricular conduction during the complete day and according to the activity. Insofar as one has all necessary information thanks to implementation of the above mentioned improvements, it is interesting to be able, e.g., to monitor the PR and AR intervals according to the hour of the day, to the atrial frequency and according to the state awake/sleep or rest/effort of the patient, and this over a period of variable duration (e.g., 24 hours, 1 week, 1 month, 3 months, or 6 months).

The durations of the PR and AR intervals in the various states (effort, rest, or sleep) are then memorized in a differentiated way, and the histograms are built over the period concerned, e.g., of the histograms of the intervals PR and AR according to the period of day or night. The episodes of disorder of conduction are memorized in the form of histograms. These histograms make it possible to bring a knowledge over the duration of the paroxystic AVB, which is unknown.

One skilled in the art will appreciate that the present invention can be practiced by other than the described embodiments, which are presented for purposes of illustration and not of limitation.

We claim:

1. An active implantable medical device comprising:
    means for detecting spontaneous atrial and ventricular events;
    means for ventricular and atrial stimulation;
    means for operating the device in AAI mode with ventricular detection;
    means for operating the device in DDD mode;
    means for mode switching,
        wherein said means for mode switching further comprises means for controlling switching from AAI mode to DDD mode when at least one of the following conditions, each of which is checked by the means for mode switching, is fulfilled:
            a) the number of atrial events followed by a ventricular detection occurring after a delay longer than a first reference duration exceeds a first predetermined number;
            b) the number of atrial events not followed by a ventricular detection exceeds a second predetermined number among a third given number of consecutive atrial events;
            c) the number of consecutive atrial events not followed by a ventricular detection exceeds a fourth predetermined number; and
            d) the interval separating two ventricular events exceeds a second reference duration; and
        wherein said means for mode switching further comprises means for controlling the return from the DDD pacing mode to AAI pacing mode according to a criteria;
    means for state detecting, further comprising means for diagnosing a temporary specific state of a patient carrying the device, including a phase of suspicion of disorder of the atrial rate of the patient and at least one of a phase of effort and a phase of sleep of the patient; and
    wherein the mode switching means further comprises means for suspending, when said means for state detecting diagnoses a phase of suspicion of disorder of the atrial rate of the patient, the checking of the conditions a) to c), while maintaining the checking of the condition d), for a length of time at least equal to a duration of the phase of suspicion of disorder of the atrial rate of the patient.

2. The device of claim 1, wherein the means for state detecting further comprises means for diagnosing a phase of cardiac decompensation of the patient.

3. The device of claim 1, wherein the means for mode switching includes a grid of counters assigned respectively to the conditions a) to d) and to each of the diagnosed temporary specific states, the corresponding counter being incremented when the respective condition is fulfilled and when the respective state is diagnosed.

4. The device of claim 3, wherein the mode switching means further comprises a grid of thresholds homologous with the grid of counters, each threshold being programmable, and are able to force the switching from AAI mode towards DDD mode when at least one of the thresholds is reached by the corresponding counter.

5. The device of claim 1, wherein the means for mode switching further comprises means, operating in response to the means for state detecting, for modifying the criteria of the return to AAI mode after switching towards DDD mode during the time when a phase of effort or sleep is diagnosed.

6. The device of claim 5, wherein the means for mode switching further comprises means, operating in response to the means for state detecting, for temporarily suspending any return to AAI mode after switching towards DDD mode during the time when a phase of effort or sleep is diagnosed.

7. The device of claim 5, wherein the means for mode switching further comprises means, operating in response to the means for state detecting, for temporarily modifying in a restrictive direction the criteria of return to AAI mode after switching towards DDD mode during the time when the phase of effort or sleep is diagnosed.

8. The device of claim 7, wherein the means for mode switching further comprises means operating in response to the means for state detecting, for controlling without delay the return to AAI mode after switching towards DDD mode after the end of the phase of effort or sleep.

9. The device of claim 7, wherein the means for mode switching further comprises means, operating in response to the means for state detecting, for temporarily modifying in an extensive direction the criteria of return to AAI mode after switching towards DDD mode after the end of the phase of effort or sleep.

10. The device of claim 1, further comprising:
    a criteria of durable commutation to DDD mode; and
    wherein the means for mode switching further comprises means for durable commutation, able to inhibit the return of DDD mode to AAI mode and to force the operating mode to DDD mode in function of the criteria of durable commutation to DDD mode.

11. The device of claim 10, wherein the means for durable commutation further comprises means for selectively incrementing counters, corresponding to the conditions a) to d), when the respective condition is fulfilled, wherein the means for mode switching inhibits the return of DDD mode to AAI mode and forces the operating mode to DDD mode when the counters reach a predetermined configuration of counting.

12. The device of claim 11, wherein the means for durable commutation is able to inhibit the incrementing of the counters when one of the conditions a) to c) is fulfilled while authorizing the incrementing when the condition d) is fulfilled, in the event of commutation consecutive to a diagnosis of phase of effort or sleep.

13. The device of claim 11, wherein the means for durable commutation is able to inhibit the incrementing of the counters in the event of the occurrence of a commutation separated from the preceding commutation by a number of cycles in AAI mode lower than a fifth predetermined number.

14. The device of claim 10, wherein the means for durable commutation is able to inhibit the return of DDD mode to AAI mode and to force the operating mode to DDD mode when the number of commutations of AAI mode towards DDD mode is higher than a sixth number predetermined over a first predetermined temporal period.

15. The device of claim 10, wherein the means for durable commutation is able to inhibit the return of DDD mode to AAI mode and to force the operating mode to DDD mode when the percentage of ventricular events stimulated over a second predetermined temporal period is higher than a first predetermined threshold.

16. The device of claim 10, wherein the means for durable commutation further comprises means for controlling the return to the operating mode in AAI mode at the end of each phase of sleep.

17. The device of claim 11, wherein the means for durable commutation further comprises means for reinitialing the counters at the end of each phase of sleep.

18. The device of claim 10, further comprising:
a criteria of final commutation in DDD mode; and
wherein the means for mode switching further comprises means for final commutation, able to prohibit the return from DDD mode to AAI mode and to impose an operating DDD mode until reprogramming of the device, as a function of the criteria of final commutation in DDD mode.

19. The device of claim 18, wherein the means for final commutation is able to prohibit the return from DDD mode to AAI mode and to impose an operating DDD mode until reprogramming of the device when a number of durable commutations of AAI mode towards DDD mode is higher than a seventh predetermined number over a third predetermined temporal period.

20. The device of claim 18, wherein the means for final commutation is able to prohibit the return of DDD mode to AAI mode and to impose an operating DDD mode until reprogramming of the device when a percentage of ventricular events stimulated over a fourth predetermined temporal period is greater than a second predetermined threshold.

21. The device of claim 1, wherein the means for mode switching reduces a first duration of reference during a time when a phase of effort is diagnosed.

22. The device of claim 21, wherein the means for mode switching reduces a first duration of reference to a value which is an inverse function of a frequency of stimulation.

23. The device of claim 22, wherein the inverse function of a frequency of stimulation is a decreasing monotonic function from a base frequency of stimulation to a maximum frequency of stimulation.

24. The device of claim 22, wherein the inverse function of a frequency of stimulation is a decreasing monotonic function between a low frequency, higher than a base frequency of stimulation, and a high frequency, higher than a maximum frequency of stimulation, and a constant function below the base frequency of stimulation and above the maximum frequency of stimulation.

25. The device of claim 1, further comprising means for differentiated recording of cardiac data, further comprising means for memorizing specifically predetermined data during a time when a temporary specific state is diagnosed.

26. The device of claim 25, wherein the predetermined data memorized by the means for differentiated recording includes values of durations of atrio-ventricular conduction.

27. The device of claim 25, wherein the predetermined data memorized by the means for differentiated recording includes each duration of an episode during which commutations follow one another separated from each other by a number of cycles in AAI mode lower than a fifth predetermined number.

* * * * *